(12) United States Patent
Van Amsterdam et al.

(10) Patent No.: US 6,509,340 B1
(45) Date of Patent: Jan. 21, 2003

(54) AMIDE AND UREA DERIVATIVES AS 5-HT REUPTAKE INHIBITORS AND AS 5-HT1B/1D LIGANDS

(75) Inventors: Christoph Van Amsterdam, Darmstadt (DE); Hartmut Greiner, Weiterstadt (DE); Henning Boettcher, DArmstadt (DE); Gerd Bartoszyk, Weiterstadt (DE); Juergen Harting, Darmstadt (DE); Lisa Matzen, Mainz (DE); Wilfried Rautenberg, Reinheim (DE)

(73) Assignee: Merck Patentgesellschaft, Darmstadt (DE)

( * ) Notice: Subject to any disclaimer, the term of this patent is extended or adjusted under 35 U.S.C. 154(b) by 0 days.

(21) Appl. No.: 09/868,840

(22) PCT Filed: Dec. 22, 1998

(86) PCT No.: PCT/EP98/08457

§ 371 (c)(1),
(2), (4) Date: Oct. 3, 2001

(87) PCT Pub. No.: WO00/37456

PCT Pub. Date: Jun. 29, 2000

(30) Foreign Application Priority Data

Dec. 17, 1997 (DE) .......................... 197 56 036

(51) Int. Cl.$^7$ ...................... A61K 31/40; C07D 401/04; C07D 209/14; C07D 401/06; C07D 401/14
(52) U.S. Cl. ..................... 514/252.11; 514/253.09; 514/254.09; 544/357; 544/364; 544/373
(58) Field of Search ................................. 544/364, 357, 544/373; 514/253.09, 252.11, 254.09

(56) References Cited

FOREIGN PATENT DOCUMENTS

| DE | 19615232 | 10/1997 |
|----|----------|---------|
| EP | 0548813  | 6/1993  |
| WO | 97/14689 | 4/1997  |

OTHER PUBLICATIONS

Gennaro, AR. Remington's Pharmaceutical Sciences, 17th Edition, 1985, Mack Publishing Co., Easton, PA.*

* cited by examiner

Primary Examiner—Bruck Kifle
(74) Attorney, Agent, or Firm—Millen, White, Zelano & Branigan, P.C.

(57) ABSTRACT

Amide and urea derivatives of the formula I

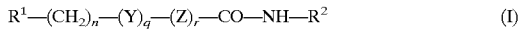

$$R^1-(CH_2)_n-(Y)_q-(Z)_r-CO-NH-R^2 \quad (I)$$

in which $R^1$, n, Y, q, Z, r and $R^2$ have the meanings indicated in Claim 1, are potent 5-$HT_{1B/1D}$ antagonists and exhibit 5-HT reuptake-inhibiting actions and are suitable for the treatment and prophylaxis of anxiety states, depressions, schizophrenia, compulsive ideas, tardive dyskinesias, learning disorders, age-dependent memory disorders, for positively affecting obsessive-compulsive behaviour (OCD), and also for the treatment and for the control of the sequelae of cerebral infarcts such as stroke and cerebral ischaemias.

10 Claims, No Drawings

AMIDE AND UREA DERIVATIVES AS 5-HT REUPTAKE INHIBITORS AND AS 5-HT1B/1D LIGANDS

The invention relates to amide and urea derivatives of the formula I

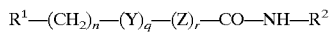

$R^1$—$(CH_2)_n$—$(Y)_q$—$(Z)_r$—CO—NH—$R^2$   I in which
$R^1$ is 3-indolyl which is unsubstituted or mono- or disubstituted by A, AO, OH, Hal, CN, $NO_2$, $NH_2$, NHA, $NA_2$, COA, $CONH_2$, CONHA, $CONA_2$, $CH_2OH$, $CH_2OA$, $CH_2NH_2$, $CH_2NHA$, $CH_2NA_2$, COOH and/or COOA,
$R^2$ is

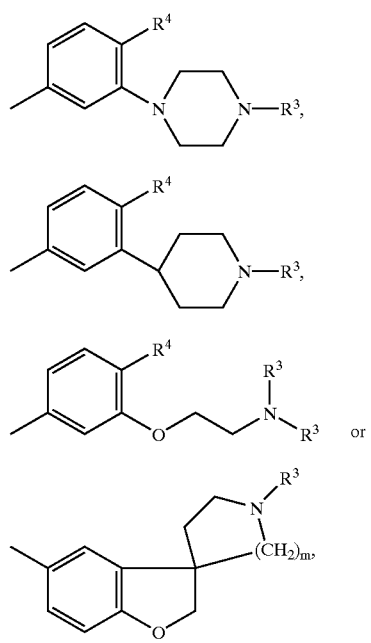

m is 1 or 2,
n is 0, 1, 2, 3 or 4,
Y is a 1,4-cyclohexylene, 1,3-pyrrolidinylene, 1,4-piperazinylene or 1,4-piperidinylene ring, which can also be partially dehydrogenated,
Z is $(CH_2)_n$ or $(CH_2)_nNH$—,
q is 0 or 1,
r is 0 or 1,
$R^3$ is A,
$R^4$ is AO,
Hal is F, Cl, Br or I,
A is straight-chain or branched alkyl having 1–6 C atoms,
with the proviso that q and r are not simultaneously 0, and their physiologically acceptable salts.

The invention was based on the object of finding novel compounds having useful properties, in particular those which can be used for the production of medicaments.

It has been found that the compounds of the formula I and their physiologically acceptable acid addition salts have useful pharmacological properties together with good tolerability, since they have effects on the central nervous system. The compounds especially affect serotoninergic transmission by inhibiting the reuptake of serotonin (5-HT) and having a strong affinity for $5\text{-}HT_{1B/1D}$ receptors. As a result of these combined activities, they are particularly suitable as antidepressants and anxiolytics.

The compounds exhibit 5-HT-agonistic and antagonistic properties as well as a 5-HT reuptake-inhibiting action. For the in-vitro demonstration of the inhibition of reuptake of 5-HT, inhibition of synaptosomal uptake is used (Wong et al., Neuropsycho-pharmacology 8 (1993), 22–33). Ex vivo, this property is investigated in mouse brain tissue according to a method of Waldmeier (European J. Pharmacol. 46 (1997), 387–392). The affinity for $5\text{-}HT_{1B/1D}$ receptors can be determined, for example, by the methods described by Peroutka et al. (Synapse 3 (1983), 61–66) and Hoyer et al. (European J. Pharmacol. 118 (1985), 1–12) and $5\text{-}HT_{1B/1D}$-antagonistic properties can be determined by a method of Choppin et al. (British Journal of Pharmacology, 114 (1995), 309–314).

Similar compounds which likewise exhibit $5\text{-}HT_{1B/1D}$ [sic] antagonistic [sic] actions are described, for example, in the Patent Applications WO 97/14689 or WO 97/41802.

The compounds of the formula I are therefore suitable both in veterinary and in human medicine for the treatment of functional disorders of the central nervous system and of inflammation. They can be used for the prophylaxis and for the control of the sequelae of cerebral infarcts (cerebral apoplexy) such as stroke and cerebral ischaemias, and for the treatment of extrapyramidal motor side effects of neuroleptics and also of Parkinson's disease, for the acute and symptomatic therapy of Alzheimer's disease and also for the treatment of amyotrophic lateral sclerosis. They are likewise suitable as therapeutics for the treatment of cerebral and spinal cord traumata. In particular, however, they are suitable as pharmaceutical active compounds for anxiolytics, antidepressants, anti-psychotics, neuroleptics, antihypertensives and/or for positively affecting obsessive-compulsive disorder (OCD), anxiety states, panic attacks, psychoses, anorexia, delusional ideas, agoraphobia, migraine, Alzheimer's disease, sleep disorders, tardive dyskinesias, learning disorders, age-dependent memory disorders, eating disorders such as bulimia, drug abuse and/or sexual function disorders.

In addition, they are suitable for the treatment of endocrine disorders such as hyperprolactinaemia, and further in vasospasms, hypertension and gastro-intestinal disorders. They can furthermore be employed as intermediates for the production of other pharmaceutical active compounds.

The invention relates to amide and urea derivatives of the formula I, and their physiologically acceptable acid addition salts.

The invention relates in particular to compounds of the formula I selected from the group consisting of
a) N-[2-(5-fluoro-3-indolyl)ethyl]-N'-[4-methoxy-3-(4-methyl-1-piperazinyl)phenyl]urea;
b) 4-(5-cyano-3-indolyl)-N-[4-methoxy-3-(4-methylpiperazin-1-yl)phenyl]piperidine-1-carboxamide;
c) 4-(6-fluoro-3-indolyl)-N-[4-methoxy-3-(4-methylpiperazin-1-yl)phenyl]piperidine-1-carboxamide;
d) 3-{1-[4-methoxy-3-(4-methyl-1-piperazinyl)phenylaminocarbonyl]-4-piperidyl}indole-5-carboxamide;
e) 4-(5-fluoro-3-indolyl)-N-[4-methoxy-3-(4-methylpiperazin-1-yl)phenyl]piperidine-1-carboxamide;

f) 4-[2-(3-indolyl)ethyl]-N-[4-methoxy-3-(4-methylpiperazin-1-yl)phenyl]piperidine-1-carboxamide;

g) 4-(3-indolyl)-N-[4-methoxy-3-(4-methylpiperazin-1-yl)phenyl]piperidine-1-carboxamide;

h) 4-(4-fluoro-3-indolyl)-N-[4-methoxy-3-(4-methylpiperazin-1-yl)phenyl]piperidine-1-carboxamide;

i) 4-(7-methoxyindol-3-yl)piperidine-1-carboxylic acid [4-methoxy-3-(4-methylpiperazin-1-yl)phenyl]-amide;

j) 4-[4-(5-fluoro-3-indolyl)butyl]piperazine-1-carboxylic acid [4-methoxy-3-(4-methylpiperazin-1-yl)phenyl] amide;

k) 4-(5-cyanoindol-3-yl)-3,6-dihydro-2H-pyridine [lacuna] 1-carboxylic acid [4-methoxy-3-(4-methylpiperazin-1-yl)phenyl]amide;

l) 3-(5-fluoroindol-3-yl)pyrrolidine-1-carboxylic acid [4-methoxy-3-(4-methylpiperazin-1-yl)phenyl]-amide;

m) 4-(5-fluoroindol-3-yl)cyclohexanecarboxylic acid [4-methoxy-3-(4-methylpiperazin-1-yl)phenyl]amide;

n) N-[2-(5-hydroxy-3-indolyl)ethyl]-N'-[4-methoxy-3-(4-methyl-1-piperazinyl)phenyl]urea;

o) N-{2-[4-(6-fluoro-3-indolyl)piperidin-1-yl]ethyl}-N'-[4-methoxy-3-(4-methyl-1-piperazinyl)phenyl]-urea;

p) N-[4-(5-cyano-3-indolyl)butyl]-N'-[4-methoxy-3-(4-methyl-1-piperazinyl)phenyl]urea;

q) 4-[4-(5-cyano-3-indolyl)butyl]piperazine-1-carboxylic acid [4-methoxy-3-(4-methyl-1-piperazinyl)-phenyl] amide;

r) 4-(5-fluoroindol-3-yl)piperidine-1-carboxylic acid (2,3-dihydro-1'-methylspiro(benzofuran)-3,4-piperidin)amide;

s) N-{2-[4-(6-fluoro-3-indolyl)piperidin-1-yl]ethyl}-[2,3-dihydro-1-methylspiro(benzofuran)-3,4-piperidin]urea;

and their physiologically acceptable salts.

The invention accordingly relates to the compounds of the formula I and to a process for the preparation of compounds of the formula I according to Claim 1.

The preparation process is characterized in that a) a compound of the formula II

$$H_2N—R^2 \qquad\qquad II$$

in which $R^2$ has the meaning indicated in Claim 1, is reacted with a compound of the formula III

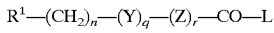

$$R^1—(CH_2)_n—(Y)_q—(Z)_r—CO—L \qquad\qquad III$$

in which L is Cl, Br, I, OH or another reactively [sic] functionally modified OH group or easily nucleophilically substitutable leaving group and $R^1$, n, Y, q, Z and r have the meanings indicated in Claim 1, or b) the amine component of the formula II

$$H_2N—R^2 \qquad\qquad II$$

is reacted with the component of the formula IV

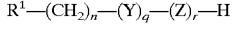

$$R^1—(CH_2)_n—(Y)_q—(Z)_r—H \qquad\qquad IV$$

in which $R^1$, $R^2$, n, Y, q, Z and r have the meanings indicated, with addition of coupling reagents such as N,N'-carbonyldiimidazole, diphosgene, triphosgene or alternatively chloroformic acid esters, and/or c) in that one of the radicals $R^1$, $R^3$ and/or $R^4$ is optionally converted into another radical $R^1$, $R^3$ and/or $R^4$ by, for example, cleaving an OA group with formation of an OH group and/or derivatizing a CN, COOH or COOA group and/or in that, for example, a primary or secondary N atom is alkylated and/or in that a base or acid of the formula I which is obtained is converted into one of its salts by treating with an acid or base.

The invention likewise relates to medicaments comprising compounds of the formula I and their physiologically acceptable salts having 5-HT1B/D-antagonistic [sic] and 5-HT reuptake-inhibiting action.

The invention relates to the compounds of the formula I and to their enantiomers and diastereomers and their salts.

For all radicals which occur two or more times, such as, for example, A or $R^3$, it is a condition that their meanings are independent of one another.

The radical A is alkyl and has 1 to 6, preferably 1, 2, 3 or 4, in particular 1 or 2 C atoms. Alkyl is therefore in particular, for example, methyl, furthermore ethyl, n-propyl, isopropyl, n-butyl, sec-butyl or tert-butyl, and further also pentyl, 1-, 2- or 3-methylbutyl, 1,1-, 1,2- or 2,2-dimethylpropyl, 1-ethylpropyl, hexyl, 1-,2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methoxypropyl, 1,1,2- or 1,2,2-trimethylpropyl.

OA is preferably methoxy, and further also ethoxy, n-propoxy, isopropoxy, n-butoxy, isobutoxy, sec-butoxy or tert-butoxy.

NHA is preferably methylamino, further ethylamino, isopropylamino, n-butylamino, isobutylamino, sec-butylamino or tert-butylamino. $NA_2$ is preferably dimethylamino, further N-ethyl-N-methylamino, diethylamino, di-n-propylamino, diisopropylamino or di-n-butylamino. Resulting from this, CO-NHA is preferably N-methylcarbamoyl or N-ethylcarbamoyl; $CO-NA_2$ is preferably N,N-dimethylcarbamoyl or N,N-diethylcarbamoyl.

Hal is preferably fluorine, chlorine, bromine or iodine, in particular fluorine or chlorine.

n is 0, 1, 2, 3 or 4, in particular 0, 2 or 4.

The radical $R^3$ is in each case independently of one another A, it being possible for the two radicals $R^3$ in formula (Ic) to be identical or different. Preferably, they are both identical and are in particular preferably methyl.

Y is preferably a 1,4-piperazinylene or 1,4-piperidinylene ring, which can also be partially dehydrogenated and is then preferably a 1,4-substituted 3,6-dihydro-2H-pyridine ring, and further also a 1,3-pyrrolidinylene or 1,4-cyclohexylene ring.

$R^1$ is preferably 2- or 3-indolyl which is unsubstituted or mono- or disubstituted, but in particular monosubstituted, by Hal, CN, A, AO, $CONH_2$, CONHA, $CONA_2$, COOH, COOA, $CH_2Ar$, $CH_2OAr$ and/or $CH_2NA_2$, 3-indolyl being particularly preferred. The indole radical is preferably substituted in the 5-position, and further also in the 4-, 6- or 7-position.

$R^1$ is therefore particularly preferably 3-indolyl, 5- or 6-methylindol-3-yl, 5- or 6-methoxyindol-3-yl, 5- or 6-hydroxyindol-3-yl, 4-, 5- or 6-fluoroindol-2-yl, 4-, 5- or 6-fluoroindol-3-yl, 5- or 6-cyanoindol-3-yl, 5- or 6-chloroindol-3-yl, 5- or 6-carboxyindol-3-yl, 5- or 6-methoxycarbonylindol-3-yl, 5- or 6-hydroxyindol-3-yl, 5- or 6-hydroxymethylindol-3-yl, 5- or 6-aminomethylindol-2-yl, 5- or 6-aminomethylindol-3-yl, and also 5- or 6-bromoindol-3-yl, 5-or 6-ethylindol-3-yl, 5- or 6-isopropylindol-3-yl, 5- or 6-dimethylaminoindol-3-yl or 5- or 6-ethoxyindol-3-yl.

R is (Ia), (Ib), (Ic) or (Id). Very particularly preferred compounds here are those which contain the groups [sic] (Ia), (Ic) or (Id) as $R^2$.

m is preferably 1 or 2, preferably 2.

Z is $(CH_2)_n$ or $(CH_2)_n NH-$, n preferably being 2 or 4.

q and r are in each case 0 or 1, the proviso applying that q and r cannot simultaneously both be 0.

For the entire invention, it is a condition that all radicals which can occur two or more times in a molecule can be identical or different, i.e. are independent of one another.

The invention accordingly relates in particular to those compounds of the formula I in which at least one of the radicals mentioned has one of the preferred meanings indicated above. Some preferred groups of compounds can be expressed by the formulae I1 to I12 below, which correspond to the formula I and in which the radicals not designated in greater detail have the meaning indicated in the formula I, but in which in I1 $R^2$ is the group (Ia);

in I2 $R^2$ has a meaning indicated in I1 and $R^4$ is a methoxy radical and $R^3$ is a methyl radical;

in I3 $R^2$ is the group (Id);

in I4 $R^2$ has the meaning indicated in I3 and the radical $R^3$ is a methyl group;

in I5 $R^2$ is the group (Ib) or (Ic);

in I6 q=1 and r=0;

in I7 $R^1$ is indol-3-yl monosubstituted by CN, F, OA, $CONH_2$ or OH;

in I8 q=0 and r=1;

in I9 q and r have the meaning indicated in I6 and Y is a 1,4-piperidinylene ring;

in I10 q and r have the meaning indicated in I6 and Y is a 1,4-cyclohexylene or 1,4-piperazinylene ring;

in I11 q and r have the meaning indicated in I8 and n is 2 or 4;

in I12 q=r=1.

The compounds of the formula I and also the starting substances for their preparation are otherwise prepared by methods known per se, such as are described in the literature (e.g. in standard works such as Houben-Weyl, Methoden der Organischen Chemie [Methods of Organic Chemistry], Georg Thieme Verlag, Stuttgart; Organic Reactions, John Wiley & Sons, Inc., New York), namely under reaction conditions which are known and suitable for the reactions mentioned. Use can also be made here of variants which are known per se and are not mentioned here in greater detail.

If desired, the starting substances for the process claimed can also be formed in situ in such a way that they are not isolated from the reaction mixture, but immediately reacted further to give the compounds of the formula I. On the other hand, it is possible to carry out the reaction stepwise.

In the compounds of the formula III, the radical L is preferably Cl or Br; but it can also be I, OH or alternatively preferably a reactively [sic] functionally modified OH group, in particular alkylsulfonyloxy having 1–6 (e.g. methanesulfonyloxy) or arylsulfonyloxy having 6–10 C atoms (e.g. benzenesulfonyloxy, p-toluenesulfonyloxy, 1- or 2-naphthalenesulfonyloxy) or alternatively trichloromethoxy, alkoxy, such as, for example, methoxy, ethoxy, propoxy or butoxy, and further also phenoxy.

The compounds of the formula I can preferably be obtained by reacting compounds of the formula II with compounds of the formula III.

As a rule, the starting substances of the formulae II and III are known; the unknown compounds of the formulae II and III can easily be prepared analogously to the known compounds.

The compounds of the formula III can also be prepared from known compounds, for example also by electrophilic substitution or, in certain cases, also nucleophilic aromatic substitution. A suitable starting substance here is often the corresponding indole-3-alkanoic acid (which can be prepared analogously to a Japp-Klingemann type Fischer indole synthesis, cf. for this Böttcher et al., J. Med. Chem. 1992, 35, 4020–4026 or Iyer et al., J. Chem. Soc. Perkin Trans. II 1973, 872–878), which, if required, can be reduced further and substituted.

The reaction of the compounds II and III proceeds according to methods such as are known from the literature for the alkylation or acylation of amines. However, it is also possible to react the compounds in the presence of an indifferent solvent. Suitable solvents are, for example, hydrocarbons, such as benzene, toluene, xylene; ketones such as acetone, butanone; alcohols such as methanol, ethanol, isopropanol, N-butanol [sic]; ethers such as tetrahydrofuran (THF) or dioxane; amides such as dimethylformamide (DMF) or N-methylpyrrolidone; nitrites such as acetonitrile, and, if appropriate, also mixtures of these solvents with one another or mixtures with water. The addition of an acid-binding agent, for example of an alkali metal or alkaline earth metal hydroxide, carbonate or bicarbonate or of another salt of a weak acid of the alkali metals or alkaline earth metals, preferably of potassium, sodium or calcium, or the addition of an organic base such as triethylamine, dimethylaniline, pyridine or quinoline or an excess of piperazine derivative of the formula II may be favourable. Depending on the conditions used, the reaction time is between a few minutes and 14 days, and the reaction temperature is between approximately 0 and 150°, normally between 20 and 130°.

It may be necessary before carrying out this reaction to protect further amino groups contained from an alkylation or acylation by introduction of suitable protective groups. The expression amino protective group is generally known and relates to groups which are suitable for protecting an amino group from chemical reactions, but which are easily removable after the desired reaction has been carried out at another position in the molecule. Since such protective groups and the introduction and removal of these are well known to the person skilled in the art from numerous references and text books, it is not necessary to go into these in greater detail here.

In addition, compounds of the formula I can be prepared by reacting amines of the formula II with a component of the formula IV containing the radical $R^1$.

As a rule, the respective components are known or can be prepared according to known processes, as already described.

The preparation of compounds of the formula II in which $R^2$ is the radical Ia (piperazine derivatives) is also described, for example, by Clitherow, J. W. et al., in J. Med. Chem 1994, 37 (15), 2253–2257. The compounds of the formula II in which $R^2$ is Ib (piperidine derivatives) are likewise disclosed, for example in WO 96/31508.

The spiro compounds of the formula II where $R^2$ is Id are disclosed in WO 96/19477 and the compounds of the formula II in which $R^2$ is the radical Ic are disclosed in WO 95/26328.

The compounds of the formula [sic] II and IV are then carried out [sic] with the aid of coupling reagents, such as, for example, N,N'-carbonyldiimidazole, diphosgene or triphosgene or alternatively chloroformic acid esters. This synthesis is carried out according to the customary conditions of an acylation, as already described. Preferably, this coupling is carried out at room temperature here using N,N-carbonyldiimidazole, triethylamine and acetonitrile as an indifferent solvent.

Moreover, it is possible to carry out certain reductions by use of $H_2$ gas with catalytic action of transition metals, such as Raney Ni or Pd. It is possible in this manner to replace, for example, Cl, Br, I, SH or, in certain cases, also OH groups by hydrogen. Nitro groups can likewise be converted into $NH_2$ groups by catalytic hydrogenation with $Pd/H_2$ in methanol.

Compounds which otherwise correspond to the formula I, but instead of one or more H atoms contain one or more solvolysable group(s) can be solvolysed, in particular hydrolysed, to the compounds of the formula I.

Furthermore, a compound of the formula I can be converted into another compound of the formula I by methods known per se.

Compounds of the formula I in which $R^1$ is an indole radical which is substituted by $CONH_2$, CONHA or $CONA_2$ can be obtained by derivatization of appropriate substituted compounds of the formula I by partial hydrolysis. It is further possible to hydrolyse cyano-substituted compounds of the formula I first to acids and to amidate the acids using primary or secondary amines. The reaction of the free carboxylic acid with the amine is preferably carried out under the conditions of a peptide synthesis. This reaction preferably takes place in the presence of a dehydrating agent, e.g. of a carbodiimide such as dicyclohexylcarbodiimide or N-(3-dimethylaminopropyl)-N-ethylcarbodiimide, furthermore propanephosphonic anhydride (cf. Angew. Chem. 92, 129 (1980)), diphenylphosphoryl azide or 2-ethoxy-N-ethoxycarbonyl-1,2-dihydroquinoline, in an inert solvent, e.g a halogenated hydrocarbon such as dichloromethane, an ether such as THF or dioxane, an amide such as DMF or dimethylacetamide, a nitrile such as acetonitrile, at temperatures between approximately –10 and 40°, preferably between 0 and 30°. Instead of the acid or of the amide, it is also possible to employ reactive derivatives of these substances in the reaction, e.g. those in which reactive groups are intermediately blocked by protective groups. The acids can also be used in the form of their activated esters, which are expediently formed in situ, e.g. by addition of 1-hydroxybenzotriazole or N-hydroxysuccinimide.

It is particularly favourable, however, to prepare the nitrites in the reverse manner, by dehydration, starting from the amides, e.g. by means of trichloroacetyl chloride/$Et_3N$ [Synthesis (2), 184 (1985)] or using $POCl_3$ (J. Org. Chem. 26, 1003 (1961))

A base of the formula I obtained can be converted into the associated acid addition salt using an acid. Acids which yield physiologically acceptable salts are suitable for this reaction. Thus inorganic acids can be used, e.g. sulfuric acid, hydrohalic acids such as hydrochloric acid or hydrobromic acid, phosphoric acids such as orthophosphoric acid, nitric acid, sulfamic acid, and furthermore organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids and laurylsulfuric acid.

If desired, the free bases of the formula I can be set free from their salts by treatment with strong bases such as sodium or potassium hydroxide, or sodium or potassium carbonates, if no other acidic groups are present in the molecule. In those cases where the compounds of the formula I have free acid groups, salt formation can also be achieved by treatment with bases. Suitable bases are alkali metal hydroxides, alkaline earth metal hydroxides or organic bases in the form of primary, secondary or tertiary amines.

The invention further relates to the use of the compounds of the formula I and/or their physiologically acceptable salts for the production of pharmaceutical preparations, in particular in a non-chemical way. In this connection, they can be brought into a suitable dose form together with at least one solid, liquid and/or semi-liquid excipient or auxiliary and, if appropriate, in combination with one or more other active compound(s).

The invention further relates to compositions, in particular pharmaceutical preparations, comprising at least one compound of the formula I and/or one of its physiologically acceptable salts.

These preparations can be employed as medicaments in human and veterinary medicine. Possible excipients are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. Tablets, coated tablets, capsules, syrups, juices, drops or suppositories, in particular, are suitable for enteral administration, solutions, preferably oily or aqueous solutions, and furthermore suspensions, emulsions or implants, are suitable for parenteral administration, and ointments, creams or powders are suitable for topical application. The novel compounds can also be lyophilized and the lyophilizates obtained used, for example, for the production of injection preparations.

The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or aromatizers. If desired, they can also contain one or more further active compounds, e.g. one or more vitamins.

The compounds of the formula I and their physiologically acceptable salts can be used in the therapeutic treatment of the human or animal body and in the control of diseases. They are suitable for the treatment of disorders of the central nervous system such as states of tension, depressions, anxiety states, schizophrenia, gastrointestinal tract disorders, nausea, tardive dyskinesias, Parkinsonism and/or psychoses and of side effects in the treatment of hypertension (e.g. with α-methyldopa). The compounds can furthermore be used in endocrinology and gynaecology, e.g. for the therapy of acromegaly, hypogonadism, secondary amenorrhoea, premenstrual syndrome, undesired puerperal lactation, and furthermore for the prophylaxis and therapy of cerebral disorders (e.g. migraine), in particular in geriatrics, similar to certain ergot alkaloids. Particularly preferably, they can also be employed as therapeutics for controlling the sequela of cerebral infarcts (cerebral apoplexy), such as stroke and cerebral ischaemias, and for the treatment of cerebral and spinal cord traumata.

In particular, however, they are suitable as pharmaceutical active compounds for anxiolytics, antidepressants, antipsychotics and/or for positively affecting obsessive-compulsive disorder (OCD), sleep disorders, tardive dyskinesias, learning disorders, age-dependent memory disorders, eating disorders such as bulimia and/or sexual function disorders.

In this case, the substances according to the invention are as a rule administered in analogy to known preparations, preferably in doses of between approximately 0.1 and 500 mg, in particular between 5 and 300 mg per dose unit. The daily dose is preferably between approximately 0.01 and 250 mg/kg, in particular between 0.02 and 100 mg/kg of body weight.

In this case the substances according to the invention are as a rule preferably administered in doses of between approximately 1 and 500 mg, in particular between 5 and 100 mg per dose unit. The daily dose is preferably between approximately 0.02 and 10 mg/kg of body weight. The specific dose for each particular patient depends, however, on all sorts of factors, for example on the efficacy of the specific compound employed, on the age, body weight, general state of health and sex, on the diet, on the time and route of administration, and on the excretion rate, pharmaceutical combination and severity of the particular disorder to which the therapy relates. Oral administration is preferred.

Above and below, all temperatures are indicated in ° C. In the examples below, "customary working up" means: if necessary, the solvent is removed, if necessary, water is added, if necessary, depending on the constitution of the final product, the mixture is adjusted to a pH of between 2 and 10 and extracted with ethyl acetate or dichloromethane, the organic phase is separated off, dried over sodium sulfate, filtered and concentrated, and the residue is purified by chromatography on silica gel and/or by crystallization.

EXAMPLE 1

A solution of 4-methoxy-3-(4-methylpiperazin-1-yl) aniline dihydrochloride (2.65 g; 9 mmol), triethylamine (4.5 ml; 31.5 mmol) and N,N'-carbonyldiimidazole (1.6 g; 10 mmol) in 125 ml of acetonitrile is stirred at room temperature for 3 hours. A suspension of 2.0 g (9 mmol) of 5-fluoro-3-piperidin-4-yl-1H-indole and 1.3 ml (9 mmol) of triethylamine in 125 ml of acetonitrile is added to the mixture and it is stirred at room temperature for a further 12 hours. After customary working up, the residue is dissolved in acetone and the hydrochloride is precipitated using 1N HCl. By recrystallization from ethanol/diethyl ether, 4-(5-fluoro-1H-indole-3-yl)piperidine-1-carboxylic acid [4-methoxy-3-(4-methylpiperazin-1-yl)phenyl]amide hydrochloride is obtained

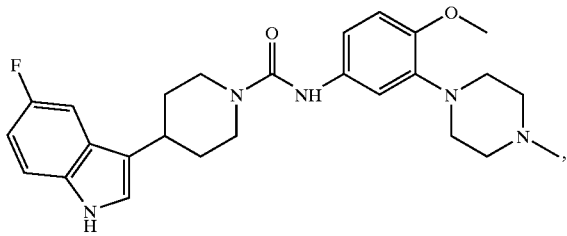

m.p. 231°.

The following are prepared analogously:
4-(3-indolyl)-N-[4-methoxy-3-(4-methyl-1-piperazinyl) phenyl]piperidine-1-carboxamide dihydrochloride, m.p. 204°;
4-(5-fluoro-1H-indol-3-yl)piperidine-1-carboxylic acid [4-methoxy-3-(N,N'-dimethylaminoethoxy)phenyl] amide;
4-(5-fluoro-1H-indol-3-yl)piperidine-1-carboxylic acid [4-methoxy-3-(4-methylpiperidin-1-yl)phenyl]amide hydrochloride;
4-(5-cyano-3-indolyl)-N-[4-methoxy-3-(4-methyl-1-piperazinyl)phenyl]piperidine [lacuna] 1-carboxamide, m.p. 194–195°;
4-(6-fluoro-3-indolyl)-N-[4-methoxy-3-(4-methyl-1-piperazinyl)phenyl]piperidine [lacuna] 1-carboxamide, m.p. 135–137°;
3-{1-[4-methoxy-3-(4-methyl-1-piperazinyl) phenylaminocarbonyl]-4-piperidyl)indole-5-carboxamide, m.p. 176–178°;
4-(4-fluoro-3-indolyl)-N-[4-methoxy-3-(4-methyl-1-piperazinyl)phenyl]piperidine [lacuna] 1-carboxamide dihydrochloride, m.p. >205° (dec.);
4-(4-fluoro-3-indolyl)-N-[4-methoxy-3-(4-methyl-1-piperidinyl)phenyl]piperidine [lacuna] 1-carboxamide dihydrochloride;
4-(7-methoxy-1H-indol-3-yl)piperidine-1-carboxylic acid [4-methoxy-3-(4-methylpiperazin-1-yl)phenyl] amide, m.p. 219–222°;
4-[2-(3-indolyl)ethyl]-N-[4-methoxy-3-(4-methyl-1-piperazinyl)phenyl]piperidine [lacuna] 1-carboxamide, m.p. 200–202°;
4-[2-(3-indolyl)ethyl]-N-[4-methoxy-3-(N,N'-dimethylaminoethoxy)phenyl]piperidine-1-carboxamide;
4-[2-(3-indolyl)ethyl]-N-[4-methoxy-3-(4-methyl-1-piperidinyl)phenyl]piperidine [lacuna] 1-carboxamide;
4-(5-cyano-3-indolyl)-3,6-dihydro-2H-pyridine-1-carboxylic acid [4-methoxy-3-(4-methyl-1-piperazinyl)phenyl]amide, m.p. 223–225°;
4-[4-(5-fluoroindol-3-yl)butyl]piperazine-1-carboxylic acid [4-methoxy-3-(4-methyl-1-piperazinyl)phenyl] amide dihydrochloride, m.p. >220° (dec.);
3-(5-fluoroindol-3-yl)pyrrolidine-1-carboxylic acid [4-methoxy-3-(4-methyl-1-piperidinyl)phenyl]amide, m.p. 210–213°;
4-(5-fluoroindol-3-yl)piperidine-1-carboxylic acid (2,3-dihydro-1'-methylspiro(benzofuran)-3,4-piperidin) amide;
4-[4-(5-cyano-3-indolyl)butyl]piperazine-1-carboxylic acid [4-methoxy-3-(4-methyl-1-piperazinyl)phenyl] amide
4-[4-(5-cyano-3-indolyl)butyl]piperazine-1-carboxylic acid [4-methoxy-3-(4-methyl-1-piperidinyl)phenyl] amide;
4-(5-cyano-1H-indol-3-yl)piperidine-1-carboxylic acid [4-methoxy-3-(N,N'-dimethylaminoethoxy)phenyl] amide;
4-(3-indolyl)piperidine-1-carboxylic acid [4-methoxy-3-(N,N'-dimethylaminoethoxy)phenyl]amide;
4-[4-(5-fluoro-1H-indol-3-yl)butyl]piperazine-1-carboxylic acid [4-methoxy-3-(N,N'-dimethylaminoethoxy)-phenyl]amide;
4-[4-(5-cyano-1H-indol-3-yl)butyl]piperazine-1-carboxylic acid [4-methoxy-3-(N,N'-dimethylaminoethoxy)phenyl]amide;
4-(5-cyano-1H-indol-3-yl)piperidine-1-carboxylic acid (2,3-dihydro-1'-methylspiro(benzofuran)-3,4-piperidin)amide

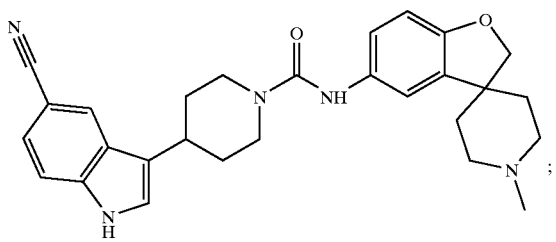

4-(3-indolyl)piperidine-1-carboxylic acid; (2,3-dihydro-1'-methylspiro(benzofuran)-3,4-piperidin)amide;

4-[4-(5-fluoro-1H-indol-3-yl)butyl]piperidine-1-carboxylic acid (2,3-dihydro-1'-methylspiro (benzofuran)-3,4-piperidin)amide;

4-[4-(5-cyano-1H-indol-3-yl)butyl]piperidine-1-carboxylic acid (2,3-dihydro-1'-methylspiro (benzofuran)-3,4-piperidin)amide;

4-[3-(1H-indol-3-yl)propyl]piperidine-1-carboxylic acid (2,3-dihydro-1'-methylspiro(benzofuran)-3,4-piperidin)amide.

EXAMPLE 2

Analogously to Example 1, by reaction of 1.17 g (4 mmol) of 4-methoxy-3-(4-methylpiperazin-1-yl)aniline dihydrochloride, 2.0 ml (14 mmol) of triethylamine and 714 mg (4.4 mmol) of N,N'-carbonyldiimidazole in 35 ml of acetonitrile with 859 mg (4 mmol) of 5-fluorotryptamine hydrochloride and 1.1 ml (8 mmol) of triethylamine in 35 ml of acetonitrile and subsequent recrystallization from ethyl acetate/petroleum ether, N-[2-(5-fluoro-3-indolyl)ethyl]-N'-[4-methoxy-3-(4-methyl-1-piperazinyl)phenyl]urea

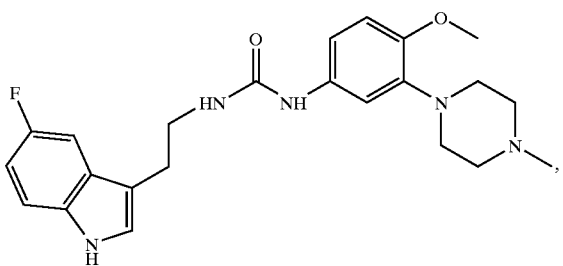

m.p. 98°.

is obtained.

The following are prepared analogously:

N-[2-(5-hydroxy-3-indolyl)ethyl]-N'-[4-methoxy-3-(4-methyl-1-piperazinyl)phenyl]urea;

N-[4-(5-cyano-3-indolyl)butyl]-N'-[4-methoxy-3-(4-methyl-1-piperazinyl)phenyl]urea;

N-[2-(5-fluoro-3-indolyl)ethyl]-N'-[4-methoxy-3-(4-methyl-1-piperidinyl)phenyl]urea;

N-[2-(5-fluoro-3-indolyl)ethyl]-N'-[4-methoxy-3-(N,N'-4-dimethylaminoethoxy)phenyl]urea;

N-{2-[4-(6-fluoro-3-indolyl)piperidin-1-yl]ethyl}-N'-[1'-methylpiperidine-3,4'-spiro-2,3-dihydrobenzofuran-5-yl]urea;

N-{2-[4-(6-fluoro-3-indolyl)piperidin-1-yl]ethyl}-N'-[4-methoxy-3-(4-methyl-1-piperazinyl)phenyl]urea, m.p. 189–192 [lacuna];

N-{2-[4-(6-fluoro-3-indolyl)piperidin-1-yl]ethyl}-N'-[4-methoxy-3-(4-methyl-1-piperidinyl)phenyl]urea;

N-{2-[4-(6-fluoro-3-indolyl)piperidin-1-yl]ethyl}-N'-[4-methoxy-3-(N,N'-4-dimethylaminoethoxy)phenyl]urea.

EXAMPLE 3

173 µl (1.2 mmol) of triethylamine and 230 mg (1.2 mmol) of 1-ethyl-3-(3-dimethylaminopropyl)-carbodiimide hydrochloride are added to a mixture of 314 mg (1.2 mmol) of 4-(5-fluoro-1H-indol-3-yl)cyclo-hexanecarboxylic acid and 265 mg (1.2 mmol) of 4-methoxy-3-(4-methylpiperazin-1-yl)aniline in 40 ml of dichloromethane. This mixture is initially stirred at 0° for one hour, then at room temperature for 12 h. The reaction mixture is concentrated, the residue is taken up in ethyl acetate, and the mixture is washed with water, 5% citric acid and sat. sodium bicarbonate solution, dried and evaporated. After column chromatographic separation, 4-(5-fluoro-1H-indol-3-yl)-cyclohexanoic acid [4-methoxy-3-(4-methylpiperazin-1-yl)phenyl]amide is obtained.

The following are prepared analogously:

4-(5-cyano-1H-indol-3-yl)cyclohexanoic acid [4-methoxy-3-(4-methylpiperazin-1-yl)phenyl]amide, 4-(6-fluoro-1H-indol-3-yl)cyclohexanoic acid [4-methoxy-3-(4-methylpiperazin-1-yl)phenyl]amide, 4-(5-fluoro-1H-indol-3-yl)cyclohexanoic acid [4-methoxy-3-(4-methylpiperidin-1-yl)phenyl]amide, 4-(5-cyano-1H-indol-3-yl)cyclohexanoic acid [4-methoxy-3-(4-methylpiperidin-1-yl)phenyl]amide, 4-(6-fluoro-1H-indol-3-yl)cyclohexanoic acid [4-methoxy-3-(4-methylpiperidin-1-yl)phenyl]amide, 4-(5-fluoro-1H-indol-3-yl)cyclohexanoic acid [4-methoxy-3-(N,N'-dimethylaminoethoxy)phenyl]amide, 2-[4-(5-fluoro-1H-indol-3-yl)piperidin-1-yl]-N-[4-methoxy-3-(4-methylpiperazin-1-yl)phenyl]acetamide, 2-[4-(5-fluoro-1H-indol-3-yl)piperidin-1-yl]-N-[3-(2-dimethylaminoethoxy)-4-methoxy-3-phenyl] acetamide, 2-[4-(1H-indol-3-yl)piperidin-1-yl]-N-[4-methoxy-3-(4-methylpiperazin-1-yl)phenyl]acetamide, 2-[4-(1H-indol-3-yl)piperidin-1-yl]-N-[3-(2-dimethylaminoethoxy-4-methoxy-3-phenyl]acetamide.

The following examples relate to pharmaceutical preparations:

EXAMPLE A

Injection Vials

A solution of 100 g of an active compound of the formula I and 5 g of disodium hydrogenphosphate in 3 l of double-distilled water is adjusted to pH 6.5 using 2N hydrochloric acid, sterile-filtered, dispensed into injection vials, lyophilized and aseptically sealed. Each injection vial contains 5 mg of active compound.

EXAMPLE B

Suppositories

A mixture of 20 g of an active compound of the formula I is fused with 100 g of soya lecithin and 1400 g of cocoa butter, poured into moulds and allowed to cool. Each suppository contains 20 mg of active compound.

EXAMPLE C

Solution

A solution is prepared from 1 g of an active compound of the formula I, 9.38 g of $NaH_2PO_4 \times 2\ H_2O$, 28.48 g of NaH$_2$PO$_4$×12 H$_2$O and 0.1 g of benzalkonium chloride in 940 ml of double-distilled water. The solution is adjusted to pH 6.8, made up to 1 land sterilized by irradiation. This solution can be used in the form of eye drops.

EXAMPLE D

Ointment 500 mg of an active compound of the formula I are mixed with 99.5 g of petroleum jelly under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is compressed to give tablets in a customary manner such that each tablet contains 10 mg of active compound.

EXAMPLE F

Coated Tablets

Analogously to Example E, tablets are pressed which are then coated in a customary manner with a coating of sucrose, potato starch, talc, tragacanth and colourant.

EXAMPLE G

Capsules 2 kg of active compound of the formula I are dispensed into hard gelatin capsules in a customary manner such that each capsule contains 20 mg of the active compound.

EXAMPLE H

Ampoules

A solution of 1 kg of active compound of the formula I in 60 l of double-distilled water is dispensed into ampoules, lyophilized under aseptic conditions and aseptically sealed. Each ampoule contains 10 mg of active compound.

What is claimed is:

1. A compound of formula I

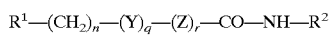    I in which

R$^1$ is 3-indolyl which is unsubstituted or mono- or disubstituted by A, AO, OH, Hal, CN, NO$_2$, NH$_2$, NHA, NA$_2$, COA, CONH$_2$, CONHA, CONA$_2$, CH$_2$OH, CH$_2$OA, CH$_2$NH$_2$, CH$_2$NHA, CH$_2$NA$_2$, COOH or COOA, R$^2$ is

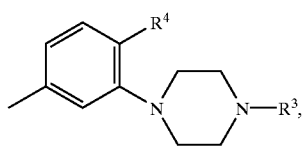    (Ia)

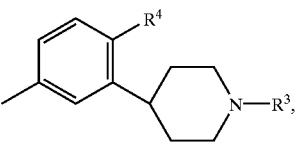    (Ib)

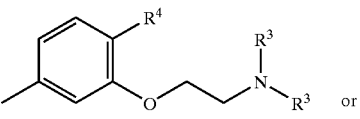    (Ic)

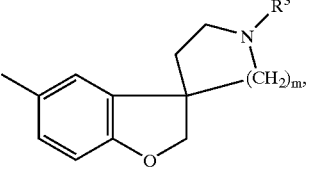    (Id)

m is 1 or 2, n is 0, 1, 2, 3 or 4,

Y is 1,4-cyclohexylene, 1,3-pyrrolidinylene, 1,4-piperazinylene or a 1,4-piperidinylene ring, which is optionally partially dehydrogenated, Z is (CH$_2$)$_n$ or (CH$_2$)$_n$NH—, q is 0 or 1, r is 0 or 1, R$^3$ is A, R$^4$ is AO, Hal is F, Cl, Br or I, A is straight-chain or branched alkyl having 1–6 C atoms, with the proviso that q and r are not simultaneously 0, or a physiologically acceptable salt thereof.

2. A process for the preparation of a compound according to claim 1, comprising a) reacting a compound of formula II

    II in which R$^2$ has the meaning indicated in claim 1, with a compound of formula III

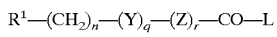    III in which

L is Cl, Br, I, OH or another reactively functionally modified OH group or easily nucleophilically substitutable leaving group, and R$^1$; n, Y, q, Z and r have the meanings indicated in claim 1, or b) reacting the amine component of formula II

    II with the compound of formula IV

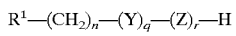    IV in which R$^1$, R$^2$, n, Y, q, Z and r have the meanings indicated in claim 1, with addition of one or more coupling reagents or c) converting one or more of the radicals R$^1$, R$^3$ or R$^4$ into another radical R$^1$, R$^3$ or R$^4$.

3. A process for the preparation of a pharmaceutical composition comprising bringing into a dose form an effective amount of a compound of claim 1 with at least one solid, liquid or semi-liquid excipient or auxiliary.

4. A pharmaceutical composition, comprising a compound of claim 1 and at least one pharmaceutically acceptable excipient or auxiliary.

5. A method of treating depression or anxiety comprising administering to a patient in need thereof a composition of claim 4.

6. A process according to claim 2, wherein the coupling regent is N,N'-carbonyldiimidazole, diphosgene, triphosgene or a chloroformic acid ester.

7. A process according to claim 2, wherein converting one or more of the radicals $R^1$, $R^3$ or $R^4$ into another radical $R^1$, $R^3$ or $R^4$ comprises cleaving an OA group with formation of an OH group, derivatizing a CN, COOH or COOA group, alkylating a primary or secondary N atom or converting a base or acid of the formula I into a salt by treating with an acid or base.

8. A compound according to claim 1, which is
a) N-[2-(5-fluoro-3-indolyl)ethyl]-N'-[4-methoxy-3-(4-methyl-1-piperazinyl)phenyl]urea,
b) 4-(5-cyano-3-indolyl)-N-[4-methoxy-3-(4-methylpiperazin-1-yl)phenyl]piperidine-1-carboxamide,
c) 4-(6-fluoro-3-indolyl)-N-[4-methoxy-3-(4-methylpiperazin-1-yl)phenyl]piperidine-1-carboxamide,
d) 3-{1-[4-methoxy-3-(4-methyl-1-piperazinyl)phenylaminocarbonyl]-4-piperidyl}indole-5-carboxamide,
e) 4-(5-fluoro-3-indolyl)-N-[4-methoxy-3-(4-methylpiperazin-1-yl)phenyl]piperidine-1-carboxamide,
f) 4-[2-(3-indolyl)ethyl]-N-[4-methoxy-3-(4-methylpiperazin-1-yl)phenyl]piperidine-1-carboxamide,
g) 4-(3-indolyl)-N-[4-methoxy-3-(4-methylpiperazin-1-yl)phenyl]piperidine-1-carboxamide,
h) 4-(4-fluoro-3-indolyl)-N-[4-methoxy-3-(4-methylpiperazin-1-yl)phenyl]piperidine-1-carboxamide,
i) 4-(7-methoxyindol-3-yl)piperidine-1-carboxylic acid [4-methoxy-3-(4-methylpiperazin-1-yl)phenyl]amide,
j) 4-[4-(5-fluoro-3-indolyl)butyl]piperazine-1-carboxylic acid [4-methoxy-3-(4-methylpiperazin-1-yl)phenyl]amide,
k) 4-(5-cyanoindol-3-yl)-3,6-dihydro-2H-pyridine-1-carboxylic acid [4-methoxy-3-(4-methylpiperazin-1-yl)phenyl]amide,
l) 3-(5-fluoroindol-3-yl)pyrrolidine-1-carboxylic acid [4-methoxy-3-(4-methylpiperazin-1-yl)phenyl]amide,
m) 4-(5-fluoroindol-3-yl)cyclohexanecarboxylic acid [4-methoxy-3-(4-methylpiperazin-1-yl)phenyl]amide,
n) N-[2-(5-hydroxy-3-indolyl)ethyl]-N'-[4-methoxy-3-(4-methyl-1-piperazinyl)phenyl]urea,
o) N-{2-[4-(6-fluoro-3-indolyl)piperidin-1-yl]ethyl}-N'-[4-methoxy-3-(4-methyl-1-piperazinyl)phenyl]urea,
p) N-[4-(5-cyano-3-indolyl)butyl]-N'-[4-methoxy-3-(4-methyl-1-piperazinyl)phenyl]urea,
q) 4-[4-(5-cyano-3-indolyl)butyl]piperazine-1-carboxylic acid [4-methoxy-3-(4-methyl-1-piperazinyl)phenyl]amide,
r) 4-(5-fluoroindol-3-yl)piperidine-1-carboxylic acid (1'-methylpiperidine-3,4'-spiro-2,3-dihydrobenzofuran-5-yl)amide,
s) N-{2-[4-(6-fluoro-3-indolyl)piperidin-1-yl]ethyl}-N'-[1'-methylpiperidine-3,4'-spiro-2,3-dihydrobenzofuran-5-yl]urea, or a physiologically acceptable salt thereof.

9. A compound according to claim 1, wherein independently of one another

A is alkyl having 1–2 carbon atoms,

Hal is F or Cl, n is 0, 2 or 4,

Y is 1,4-piperazinylene or 1,4-piperidinylene $R^1$ is 3-indolyl $R^2$ is

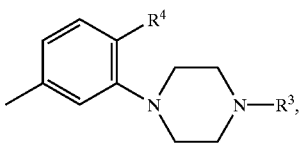
(Ia)

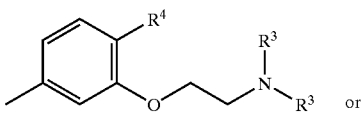
(Ic)

or

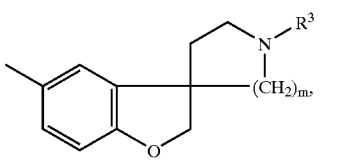
(Id)

m is 2, and n is 2 or 4.

10. A compound according to claim 1, wherein a) $R^2$ is

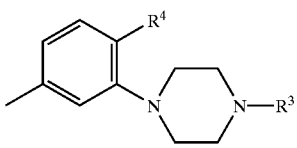
(Ia)

b) $R^2$ is

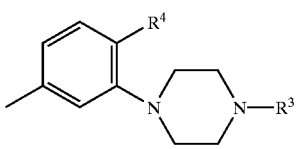
(Ia)

$R^4$ is methoxy, and
$R^3$ is methyl,
c) $R^2$ is
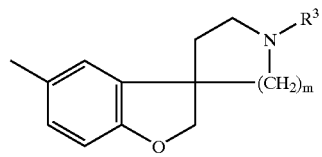
(Id)
d) $R^2$ is
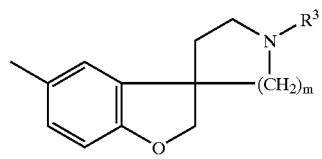
(Id)
$R^3$ is methyl,
e) $R^2$ is
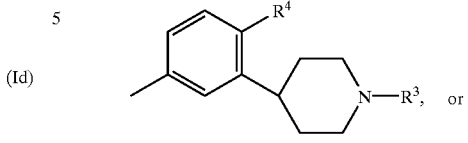
(Ib)
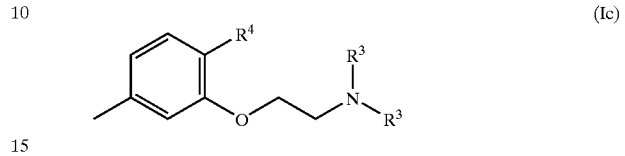
(Ic)
f) $R^1$ is indol-3-yl monosubstituted by CN, F, OA, $CONH_2$ or OH,
g) q is 1,
r is 0, and
y is 1,4-piperidinylene,
h) q is 1,
r is 0,
y is 1,4-cyclohexylene or 1,4-piperazinylene, or
i) q is 0,
r is 1, and
n is 2 or 4.
* * * * *